(12) United States Patent
Scheiblich et al.

(10) Patent No.: US 6,313,072 B1
(45) Date of Patent: Nov. 6, 2001

(54) HERBICIDAL 2-ARYLOXY-OR 2-ARYLTHIO-6-ARYLPYRIMIDINES

(75) Inventors: Stephen Scheiblich; Thomas Maier, both of Mainz; Axel Kleemann, Hanau; Helmut Siegfried Baltruschat, Schweppenhausen, all of (DE)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/252,529

(22) Filed: Feb. 18, 1999

(51) Int. Cl.$^7$ ............ C07D 239/34; C07D 239/52; A01N 43/54
(52) U.S. Cl. ............ 504/242; 504/243; 504/238; 504/235; 504/229; 504/230; 504/221; 544/295; 544/296; 544/182; 544/219; 544/55; 544/3; 544/309; 544/310; 544/316; 544/313; 544/314; 544/315; 544/317; 544/318
(58) Field of Search .................... 544/309, 310, 544/313, 314, 315, 317, 318, 316, 219, 296; 504/242, 235, 221

(56) References Cited

U.S. PATENT DOCUMENTS

| | | | | |
|---|---|---|---|---|
| 4,248,618 | * | 2/1981 | Serban ................. | 544/304 |
| 4,423,047 | * | 12/1983 | Benneche et al. ........... | 424/251 |
| 4,427,437 | * | 1/1984 | Serban ................. | 544/304 |

FOREIGN PATENT DOCUMENTS

| | | |
|---|---|---|
| 506 270 | 9/1992 | (EP) . |
| 0 723 960 | 7/1996 | (EP) . |
| 723 960 | 7/1996 | (EP) . |

OTHER PUBLICATIONS

Kroon et al, Chemical Abstract, vol. 85, entry 122887.*

* cited by examiner

*Primary Examiner*—John M. Ford
(74) *Attorney, Agent, or Firm*—Charles F. Costello

(57) ABSTRACT

The novel compounds of formula I:

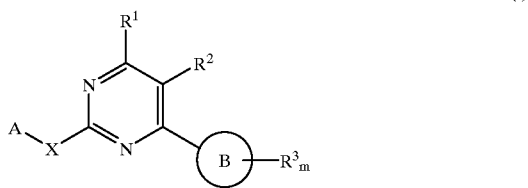

(I)

(A, B, $R^1$, $R^2$, $R^3$, X and m are defined in the specification) show selective herbicidal activity.

The new compounds can be prepared according to known methods and can be used as herbicides in agriculture and related fields.

10 Claims, No Drawings

HERBICIDAL 2-ARYLOXY- OR 2-ARYLTHIO-6-ARYLPYRIMIDINES

BACKGROUND OF THE INVENTION

Pyrimidines and their derivatives have many uses in the pharmaceutical area as well as in agriculture (herbicides, fungicides, acaricides, anthelmintics, bird repellents), as reagents, intermediates and chemicals for the polymer and textile industry.

The European patent application EP 0 723 960 A discloses for example herbicidal 2-aryl-6-aryloxypyrimidines.

Although many of the known compounds show considerable activity against various weeds, they are not completely satisfying with regard to their selectivity or because of their persistence.

The compounds according to the present invention combine high herbicidal activity with the necessary selectivity and enhanced soil degradation.

SUMMARY OF THE INVENTION

The present invention provides novel 2-aryloxy- or 2-arylthio-6-arylpyrimidines of formula I

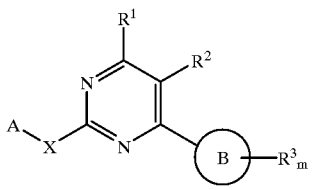

(I)

wherein
- A represents an optionally substituted aryl group or an optionally substituted 5- or 6-membered heteroaromatic group or a difluorobenzodioxolyl group;
- B represents a phenyl, pyridyl or thienyl group;
- m represents an integer from 0 to 5;
- $R^1$ represents a halogen atom or a cyano group or an optionally substituted alkyl, alkenyl, alkynyl, alkoxyalkyl, haloalkyl, alkoxy, haloalkoxy, alkylthio, alkylamino or dialkylamino group;
- $R^2$ represents a hydrogen or halogen atom or a cyano group or an optionally substituted alkyl, alkoxy, haloalkyl or haloalkoxy group;
- $R^3$ (or each $R^3$) independently represents a halogen atom, an optionally substituted alkyl, alkenyl, alkynyl, alkoxy, alkoxyalkyl, alkoxyalkoxy, alkylthio, alkylsulphinyl, alkylsulphonyl group or a nitro, cyano, haloalkyl, haloalkoxy, haloalkylthio or $SF_5$ group, and
- X represents an oxygen or sulfur atom.

The new compounds show an excellent selective herbicidal activity in certain crops, such as maize and rice, and enhanced soil degradation.

It is another object of the invention to provide methods for controlling undesired plant growth by contacting said plants with a herbicidally effective amount of the new compounds.

It is another object of the invention to provide selective herbicidal compositions containing the new compounds as active ingredients.

It is another object of the invention to provide new processes for the preparation of the new compounds.

These and other objects and features of the invention will be more apparent from the detailed description set forth hereinbelow, and from the appended claims.

DETAILED DESCRIPTION OF THE PREFERRED EMBODIMENTS

It has surprisingly been found that the novel 2-aryloxy- or 2-arylthio-6-arylpyrimidines of formula I

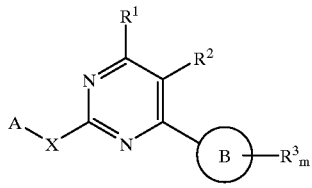

(I)

show considerable activity and high selectivity in certain crops, such as, in pre- and post-emergence applications on both broadleaf and grassy weed species.

In the definitions of the new compounds, an aryl group is suitably an optionally substituted phenyl or naphthyl group. Within the definition of A, the 5- or 6-membered heteroaryl group comprises optionally substituted 5- or 6-membered heterocycles containing one or more nitrogen and/or oxygen and/or sulfur atoms, 1 to 3 nitrogen atoms being preferred. Examples of such groups are pyrazolyl, imidazolyl, triazolyl, tetrazolyl, thienyl, pyridyl, pyrazinyl, pyrimidyl, pyridazinyl, isoxazolyl, isothiazolyl and triazinyl groups. A also includes bicyclic systems which consist of a benzene ring fused with a 5- or 6-membered heterocyclic ring as defined above. Another preferred embodiment of A is a difluorobenzodioxolyl group of formula

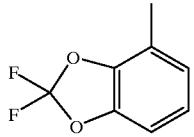

A preferably represents a phenyl, pyridyl, thienyl or pyrazolyl group being substituted by one or more of the same or different substituents selected from halogen atoms, alkyl groups, alkoxy groups, cyano groups, haloalkyl groups, haloalkoxy groups alkylthio groups, haloalkylthio groups and $SF_5$ groups, in particular wherein A has a substituent in the meta-position relative to the point of attachment. Most preferred wherein A is meta-substituted by a chlorine atom, or a trifluoromethyl, trifluoromethoxy or difluoromethoxy group.

The definition of ring B includes phenyl, 2-, 3- and 4-pyridyl and 2- and 3-thienyl groups, the phenyl, the 3-pyridyl and the 2-thienyl group are preferred, in particular the phenyl group. In a most preferred embodiment B represents a phenyl group, to which one of the substituents $R^3$ is attached in the 4-position.

Generally, if any of the above mentioned moieties comprises an alkyl, alkenyl or alkynyl group, such groups, unless otherwise specified, may be linear or branched and may contain 1 to 6, preferably 1 to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkoxy, haloalkylthio, alkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl moieties of any groups within the definitions used herein and as such can contain one or more halogen atoms. Haloalkyl, haloalkoxy and haloalkylthio are preferably fluorinated alkyl, fluorinated alkoxy and fluorinated alkylthio groups, especially trifluoromethyl, trifluoromethoxy, difluoromethoxy, difluoromethylthio, trifluoromethylthio, pentafluoroethyl or 2,2,2-trifluoroethoxy groups.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, alkylamino and dialkylamino groups, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted aryl or heteroaryl group, optional substituents include halogen, especially fluorine, chlorine and bromine atoms, and nitro, cyano, amino, hydroxyl, $C_{1-4}$-alkyl, $C_{1-4}$-alkoxy, $C_{1-4}$-haloalkyl, $C_{1-4}$-haloalkenyl, $C_{1-4}$-haloalkoxy, $C_{1-4}$-haloalkylthio and halosulfanyl groups such as $SF_5$. 1 to 5 substituents may suitably be employed, 1 to 2 substituents being preferred.

Typically haloalkyl, haloalkoxy and haloalkylthio groups are trifluoromethyl, trifluoromethoxy, difluoromethoxy, trifluoroethoxy and trifluoromethylthio groups.

m represents an integer from 0 to 5, if ring B represents a phenyl group, and an integer from 0 to 3, if ring B represents a thienyl group. Preferably m is 0, 1, 2 or 3, in particular 1 or 2, most preferred 1.

In formula I A preferably represents a group of formula a, b, c or d:

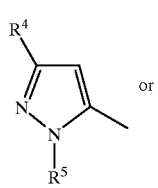
(a)

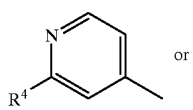
(b)

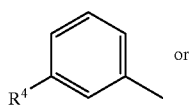
(c)

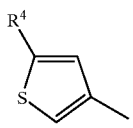
(d)

wherein
$R^5$ is $C_{1-3}$ alkyl and $R^4$ is $C_{1-4}$ alkyl, $C_{1-3}$ haloalkyl, a halogen atom, cyano, $C_{1-3}$ haloalkoxy or $C_{1-3}$ haloalkylthio; while $R^1$ is hydrogen, fluorine, chlorine, alkyl, alkoxy or alkylthio, $R^2$ is hydrogen or halogen, and $R^3$ is $C_{1-4}$ alkyl, chlorine, fluorine, trifluoromethyl, difluoromethoxy or trifluoromethoxy.

Preferred compounds of formula I are those:

wherein A represents a phenyl, pyridyl, thienyl or pyrazolyl group being substituted by one or more of the same or different substituents selected from halogen atoms, alkyl groups, alkoxy groups, haloalkyl groups, haloalkoxy groups, alkylthio groups, haloalkylthio groups and $SF_5$ groups;

wherein A has a substituent in the meta-position relative to the point of attachment; in particular wherein A is meta-substituted by a chlorine atom, or a trifluoromethyl, trifluoromethoxy or difluoromethoxy group;

wherein $R^1$ is an alkoxy group;

wherein X is oxygen;

wherein both rings A and B are substituted by at least one electro withdrawing substituent, each independently preferably selected from the group consisting of halogen atoms, haloalkyl and haloalkoxy groups, in particular fluoro, chloro, trifluoromethyl, trifluoromethoxy and difluoromethoxy;

wherein B is a phenyl group, m is 1 or 2 and one of the groups $R^3$ is attached in the para-position relative to the point of attachment; in particular the compounds of formula I A

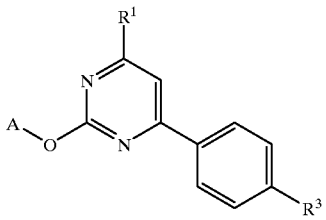
(IA)

wherein
A represents 3-trifluoromethylphenyl, 2-chloropyrid4-yl, 2-trifluoromethylpyrid-4-yl, 2-difluoromethoxypyrid-4-yl, 5-trifluoromethylthien-3-yl or 1-methyl-3-trifluoromethylpyrazol-5-yl, $R^1$ is alkyl, alkylthio or alkoxy; $R^3$ represents a fluorine, chlorine or bromine atom, or a trifluoromethyl, trifluoromethoxy, difluoromethoxy or cyano group.

The compounds according to general formula I possess a high herbicidal activity within a wide concentration range and may be used in agriculture or related fields for the selective control of undesired plants such as *Alopecurus myosuroides, Echinochloa crus-galli, Setaria viridis,*

*Galium aparine, Stellaria media, Veronica persica, Lamium purpureum, Viola arvensis, Abutilon theophrasti, Ipomoea purpurea* and *Amaranthus retroflexus* by pre- and post-emergence application, particularly in certain crops, such as maize and rice.

The following compounds have been found to be particularly effective against these weeds:
4-methoxy-2-(1'-methyl-3'-trifluoromethylpyrazol-5'-yloxy)-6-(4"-trifluoro methylphenyl)pyrimidine; 6-(4'-fluorophenyl)-4-methoxy-2-(1"-methyl-3"-trifluoromethylpyrazol-5'-yloxy)pyrimidine; 4-ethoxy-2-(1'-methyl-3'-trifluoromethylpyrazol-5'-yloxy)-6-(4"-trifluoromethylphenyl)pyrimidine; 4-methoxy-2-(3'-trifluoromethylphenoxy)-6-(4"-trifluoromethyl-phenyl) pyrimidine; 2-(2'-chloropyrid-4'-yloxy)-4-methoxy-6-(4"-trifluoromethyl-phenyl)pyrimidine; 2-(2'-difluoromethoxypyrid-4'-yloxy)-4-methoxy-6-(4"-trifluoromethyl-phenyl)pyrimidine; 2-(2'-trifluoromethylpyrid-4'-yloxy)-4-methoxy-6-(4"-trifluoromethyl-phenyl)pyrimidine; 4-methyl-2-(3'-trifluoromethylphenoxy)-6-(4"-trifluoromethyl-phenyl) pyrimidine; and 4-methoxy-2-(1'-methyl-3'-trifluoromethylpyrazol-5'-yloxy)-6-(4"-trifluoro-methylthien-2"-yl)pyrimidine.

The compounds according to the invention can be prepared by conventional methods, particularly as follows:

(A) A suitable process for the preparation of the compounds of general formula I comprises the reaction of a compound of formula III:

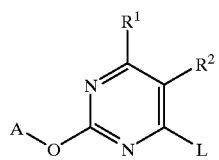

(III)

in which A, R¹, R² and n have the meaning given and L is a hydrogen atom or a leaving group, with a compound of general formula IV,

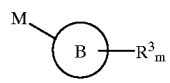

(IV)

in which
B, R³ and m have the meaning given, and
M represents a free or complexed metal preferably selected from the group consisting of Li, Mg, Zn, B, Sn,
either under the conditions of a cross coupling reaction for L being a leaving group; or
if L represents a hydrogen atom followed by an oxidation step.
M preferably represents Li, MgCl, MgBr, ZnCl, ZnBr, or B(OH)₂ or trialkyl tin.

The cross coupling reaction is carried out as a rule in the presence of a transition metal complex, as for example described in J. Org. Chem. 53 (1988) 4137, Tetrahedron 48 (1992) 8117, and Chem. Scr. 26 (1986) 305. Preferred transition metals are Pd or Ni.

(B) Alternatively a compound of formula V:

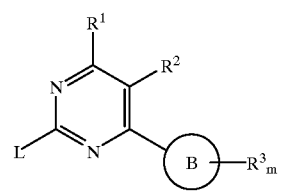

(V)

is reacted with a compound of general formula VI

A—XM¹     (VI)

wherein
A, B, R¹, R², R³, m, n and X are defined as in Claims 1 to 7;
L represents a suitable leaving group; and
M¹ represents hydrogen or a metal atom.

The reactions according to (A) and (B) may be carried out in the absence or presence of a solvent which promotes the reaction or at least does not interfere with it. Preferred are polar, aprotic or protic solvents, suitably being N,N-dimethylformamide, dimethylsulfoxide, sulfolane, acetonitrile, methyl ethyl ketone, or an ether, such as tetrahydrofurane or dioxane, or alcoholes, or water, or mixtures thereof. The reaction is carried out at a temperature between ambient temperature and the reflux temperature of the reaction mixture, preferably at elevated temperature, especially at reflux temperature.

The reactions may be carried out in the presence of a basic compound such as an alkali hydroxide, bicarbonate or carbonate, e. g. sodium or potassium hydroxide, bicarbonate or carbonate, a alkali alkoxide, e.g. sodium ethoxide, or an organic base such as triethylamine.

A hydroxy compound used in the above reactions may be present in form of a salt, preferably as a salt of an alkali metal, particularly of sodium or potassium. The presence of a copper salt may be suitable.

Suitable leaving groups L are e.g. alkyl- and arylsulfonyl, in particular methylsulfonyl or tolenesulfonyl, alkyl- and arylsulfonyloxy, perfluoroalkylsulfonyloxy, nitro and halogen, particularly fluorine, chlorine and bromine groups.

In the case of formula III L may also be a hydrogen atom, if the reaction with the compound of formula IV is followed by an oxidation step.

The compounds used as starting material are partly known or can be prepared in analogy to the known compounds using standard procedures.

Intermediates of formula III and V can be prepared by conventional methods known in pyrimidine chemistry, as described in: D. J. Brown "The Pyrimidines", in The Chemistry of Heterocyclic Compounds, Vol. 52, Eds. A. Weissberger and E. C. Taylor, John Wiley & Sons, New York—Chichester—Brisbane—Toronto—Singapore 1994. If L represents a halogen atom, III and V can for example be prepared from the corresponding hydroxy compound by reaction with a halogenating agent like POCl₃, POBr₃, PCl₅, COCl₂, SO₂Cl₂, SOCl₂. Compounds V may also be prepared by reaction of a compound of formula IV with a derivative of formula VII

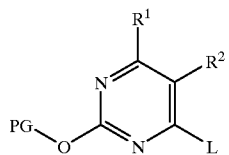
(VII)

in which

R¹, R² and L have the meaning given for formula III and PG is a protecting group which tolerates the cross-coupling with compound of formula IV and can be deprotected to yield the corresponding hydroxy compound.

In a preferred embodiment the compounds of the present invention are prepared starting from 2-alkylthio-6-halogenpyrimidines according to the following reaction scheme:

Reaction-scheme (A, B, M, L and R¹ through R³ have the meaning given, and n is an integer from 1 to 10),

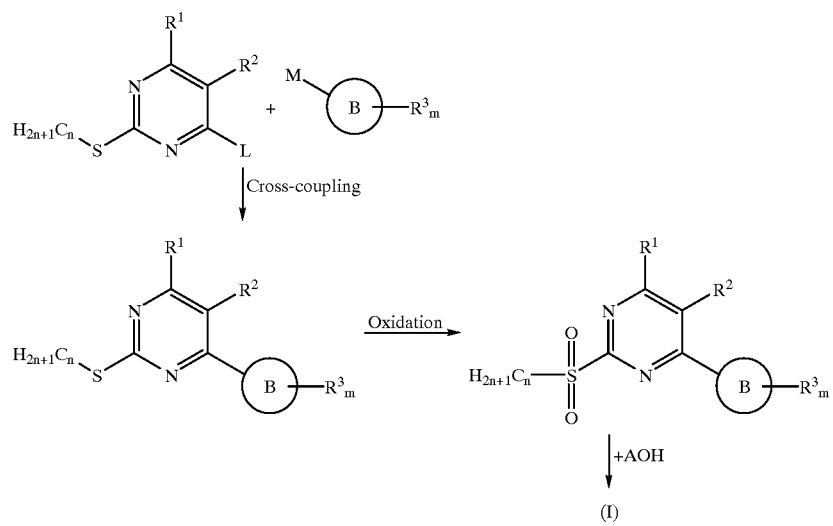

The compounds of general formula I have been found to have herbicidal activity. Accordingly, the invention further provides a herbicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and retention enhancers (stickers), and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| Compound of formula I | | 30% (w/v) |
| Emulsifier(s) | Atlox ® 4856 B and Atlox ® 4857 B[1] | 5% (w/v) |
| Solvent | Shellsol ® A[2] | to 1000 ml |

| Suspension Concentrate (SC) | | |
|---|---|---|
| Compound of formula I | | 50% (w/v) |
| Dispersing agent | Soprophor ® FL[3] | 3% (w/v) |
| Antifoaming agent | Rhodorsil ® 422[3] | 0.2% (w/v) |
| Structure agent | Kelzan ® S[4] | 0.2% (w/v) |
| Antifreezing agent | Propylene glycol | 5% (w/v) |
| Biocidal agent | Proxel ®[5] | 0.1% (w/v) |
| Water | | to 1000 ml |

| Wettable Powder (WP) | | |
|---|---|---|
| Compound of formula I | | 60% (w/w) |
| Wetting agent | Atlox ® 4995[1] | 2% (w/w) |
| Dispersing agent | Witcosperse ® D-60[6] | 3% (w/w) |
| Carrier/Filler | Kaolin | 35% (w/w) |

| Water Dispersible Granules | | |
|---|---|---|
| Compound of formula I | | 50% (w/w) |
| Dispersing/Binding agent | Witcosperse ® D-450[6] | 8% (w/w) |
| Wetting agent | Morwet ® EFW[6] | 2% (w/w) |
| Antifoaming agent | Rhodorsil ® EP 6703[3] | 1% (w/w) |
| Disintegrant | Agrimer ® ATF[7] | 2% (w/w) |
| Carrier/Filler | Kaolin | 35% (w/w) |

[1] commercially available from ICI Surfactants
[2] commercially available from Deutsche Shell AG
[3] commercially available from Rhone-Poulenc
[4] commercially available from Kelco Co.
[5] commercially available from Zeneca
[6] commercially available from Witco
[7] commercially available from International Speciality Products The compositions of this invention can also comprise other compounds having biological activity, e.g. compounds having similar or complementary pesticidal activity or compounds having plant growth regulating, fungicidal or insecticidal activity. These mixtures of pesticides can have a broader spectrum of activity than the compound of general formula I alone. Furthermore, the other pesticide can have a synergistic effect on the pesticidal activity of the compound of general formula I.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used:

2,4-D, 2,4-DB, 2,4-DP, acetochlor, acifluorfen, alachlor, alloxydim, ametrydione, amidosulfuron, asulam, atrazin, azimsulfuron, benfuresate, bensulfuron, bentazon, bifenox, bromobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl, fluazifop, fluometuron, fluoroglycofen, fluridone, fluroxypyr, flurtamone, fluthiamid, fomesafen, glufosinate, glyphosate, halosafen, haloxyfop, hexazinone, imazamethabenz, imazamethapyr, imazamox, imazapyr, imazaquin, imazethapyr, ioxynil, isoproturon, isoxaben, isoxaflutole, lactofen, MCPA, MCPP, mefenacet, metabenzthiazuron, metamitron, metazachlor, methyidimron, metolachlor, metribuzin, metsulfuron, molinate, nicosulfuron, norflurazon, oryzalin, oxadiargyl, oxasulfuron, oxyfluorfen, pendimethalin, picloram, picolinafen, pretilachlor, propachlor, propanil, prosulfocarb, pyrazosulfuron, pyridate, qinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclopyr, trifluralin.

Mixtures with other active ingredients like fungicides, insecticides, acaricides, and nematicides are possible.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The structures of the compounds prepared in the following examples were additionally confirmed by NMR and mass spectrometry.

Preparation of Intermediates

EXAMPLE A

Preparation of 3-hydroxy-5-trifluoromethylthiophene

A1 Ethyl 3-methoxy-3-trifluoromethylacrylate

Cesium carbonate (132.8 g) was added to a mixture of ethyl 4,4,4-trifluoroacetoacetate (75.0 g) and dimethylformamide (400 ml). The reaction mixture was heated to 70° C. for 30 minutes. A mixture of methyl tosylate (83.4 g) and dimethylformamide (150 ml) was added to the resulting reaction mixture within 40 minutes. The mixture was heated for 3 hours and cooled to room temperature. Upon dilution with water (800 ml) the reaction mixture was extracted with diethyl ether three times. The combined organic phases were washed with water and dried. The mixture was concentrated and the residue distilled under reduced pressure to yield the product as a clear liquid (48.5 g, 60%) with a boiling point of 62–70° C. at 12 mm.

A2 Methyl (3-hydroxy-5-trifluoromethylthien-2-yl)-carboxylate

A solution of 1M potassium hydroxide in methanol (30 ml) is added to a cooled mixture of A1 (4.6 g), methyl thioglycolate (2.46 g) and methanol (10 ml). The resulting reaction mixture was stirred for 24 hours at room temperature. Then the mixture was poured on ice and acidified with 6N sulfuric acid (pH=2). The mixture is extracted with diethyl ether twice. The combined organic phases were washed with water and dried. The mixture was concentrated and the residue is distilled under reduced pressure to yield the product as a clear liquid (3.4 g, 65%) with a boiling point of 42–45° C. at 0.10 mm.

A3 (3-Hydroxy-5-trifluoromethylthien-2-yl)-carboxylic acid

A mixture of A2 (2.38 g) and methanol (20 ml) was added to a stirred solution of sodium hydroxide (1.68 g) in water (20 ml). The reaction mixture was heated at reflux for 3 hours. The reaction mixture was cooled to room temperature and concentrated in vacuo. The concentrate was cooled to 5° C. and acidified with concentrated HCl (3.5 ml). The resulting suspension was stirred at 5° C. for 30 minutes. The solid was collected by filtration, washed with water, then dried in vacuo at 35–40° C. to give the free acid (1.45 g, 65%).

A4 3-Hydroxy-5-trifluoromethylthiophen

A3 (1.80 g) was slowly heated under argon. Evolution of gas was observed at 90° C. Heating was continued for additional 3.5 hours at 90° C. The resulting oil was distilled under reduced pressure (boiling point 70–74° C. at 4 mm) to yield 1.18 g (82%) of compound A4.

Preparation of the Compounds of Formula I

EXAMPLE 1

4-Methyl-2-methylthio-6-(4-trifluoromethylphenyl)-pyrimidine 0.236 g of 1,4-bis(diphenylphosphino)butane and 0.20 g bis(benzonitrile)-palladium(II)chloride are refluxed in 10 m toluene under nitrogen for 2 hrs. At room temperature 0.95 g 4-chloro-6-methyl-2-methylthio-pyrimidine, 1.24 g 4-trifluoromethylphenyl boronic acid, 1.38 g sodium hydrogen carbonate, 30 ml water and 40 ml dioxane are added, and the mixture is heated to reflux for 5 hrs. The organic phase is washed with water and chromatographed to give 1.15 g of the title compound.

(m.p. 77–80° C.).

EXAMPLE 2

4-Methyl-2-methylsulfonyl-6-(4-trifluoromethylphenyl)-pyrimidine

The compound from example 1 (1.05 g) is dissolved in 25 ml dry dichloromethane and 2.33 g of 60% 3-Cl-perbenzoic acid in 40 ml dichloromethane are added at room temperature. Stirring is continued over night. The solution is washed with aqueous $NaHCO_3$ and the product is purified by chromatography. Yield 1.15 g (m.p. 94–97° C.).

EXAMPLE 3

4-Methyl-2-(3-trifluoromethylphenoxy)-6-(4-trifluoromethylphenyl)-pyrimidine (Compound 1)

0.32 g of the compound from example 2 are stirred with 0.18 g 3-trifluoromethylphenol and 0.25 g potassium carbonate in 25 ml dry acetonitrile at reflux for 4 hrs. The mixture is diluted with water and extracted with ethyl acetate. 0.39 g of the title compound were isolated (m.p. 124–127° C.).

EXAMPLE 4

4-Chloro-2-methylthio-6-(4-trifluoromethylphenyl)-pyrimidine 31.3 ml 1.6M n-butyllithium in hexane are added at −70° C. to a solution of 11.25 g 4-bromo-benzotrifluorid in 50 ml diethylether. After stirring for 15 min. the solution is warmed to −30° C. and added to a −30° C. cold solution of 8.0 g 4-chloro-2-methylthio-pyrimidine in 50 ml ether. The mixture is stirred for 30 min. at −30° C. and another 30 min. at 0° C., then quenched with a mixture of 3.2 ml acetic acid, 0.5 ml water and 10 ml tetrahydrofuran (THF). Immediately after quenching, a solution of 11.8 g dichlorodicyanobenzoquinone (DDQ) in 50 ml THF is added and stirring is continued for 5 min. at room temperature. It is again cooled to 0° C. and 20 ml 10% aqueous sodium hydroxide are added. After stirring for 5 min. at 0° C. the organic layer is separated, dried and chromatographed to yield 10.3 g of the title compound (m.p. 93–96° C.).

EXAMPLE 5

2-Methylthio-4-methoxy-6-(4-trifluoromethylphenyl)-pyrimidine

A solution of 0.38 g sodium in 50 ml methanol are added to 4.6 g of the compound from example 4 in 75 ml methanol at room temperature. After stirring over night the mixture is evaporated, re-dissolved in dichloro-methane and filtered to give 4.1 g of the title product (m.p. 82–84° C.).

Analogous to the above examples the following compounds can be prepared:

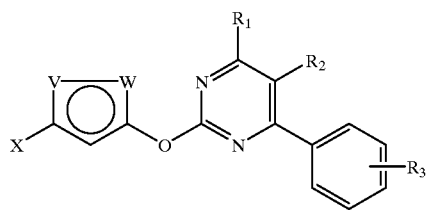

| Compound No. | X | V—W | $R_1$ | $R_2$ | $R_3$ | m.p. [° C.] |
|---|---|---|---|---|---|---|
| 1 | $CF_3$ | CH—CH—CH | Me | H | 4-$CF_3$ | 124–127 |
| 2 | $CF_3$ | N—N(Me) | Me | H | 4-$CF_3$ | 85–87 |
| 3 | Cl | N—CH—CH | Me | H | 4-$CF_3$ | 86–88 |
| 4 | $CF_3$ | CH—CH—CH | MeO | H | 4-$CF_3$ | oil |
| 5 | $CF_3$ | N—N(Me) | MeO | H | 4-$CF_3$ | 93–98 |
| 6 | Cl | N—CH—CH | MeO | H | 4-$CF_3$ | 128–131 |
| 7 | $CF_3$ | N—N(Me) | EtO | H | 4-$CF_3$ | 85–90 |
| 8 | $CF_3$ | N—CH—CH | MeO | H | 4-$CF_3$ | |
| 9 | $CHF_2O$ | N—CH—CH | MeO | H | 4-$CF_3$ | |
| 10 | $CF_3$ | N—CH—CH | MeS | H | 4-$CF_3$ | |
| 11 | $CHF_2O$ | N—CH—CH | MeS | H | 4-$CF_3$ | |
| 12 | $CF_3$ | CH—CH—CH | MeS | H | 4-$CF_3$ | |
| 13 | $CF_3$ | N—N(Me) | MeS | H | 4-$CF_3$ | |
| 14 | $CF_3$ | CH—CH—CH | Et | H | 4-$CF_3$ | |
| 15 | $CF_3$ | —S—CH— | MeO | H | 4-$CF_3$ | |
| 16 | $CF_3$ | N—N(Me) | H | Cl | 4-$CF_3$ | 73–75 |
| 17 | $CF_3$ | N—N(Me) | MeO | H | 3-$CF_3$ | 100–102 |
| 18 | $CF_3$ | N—N(Me) | MeO | H | 4-F | 110–113 |

Herbicidal Evaluation of Test Compounds

The herbicidal activity of the compounds of the present invention is evalated for the following monocotyledonous and dicotyledonous plant species:

| | Plant Species Used | |
|---|---|---|
| TRZAW | Triticum aestivum | winter wheat |
| ZEAMX | Zea mays | maize |

| | -continued | |
|---|---|---|
| | Plant Species Used | |
| GLYMA | Glycine max | soyabeans |
| GOSHI | Gossypium hirsutum | cotton |
| ORYSA | Oryza sativa | rice |
| SETVI | Setaria viridis | green foxtail |
| ABUTH | Abutilon theophrasti | velvetlaef |
| IPOHE | Ipomoea hederacea | morning glory |
| LAMPU | Lamium purpureum | deadnettle |
| MATIN | Matricaria inodora | mayweed |
| PAPRH | Papaver rhoeas | poppy |
| STEME | Stellaria media | chickweed |
| VERPE | Veronica persica | speedwell |
| CASOB | Cassia obtusifolia | sicklepod |
| GALAP | Galium aparine | cleavers |

Pre-emergence Evaluation of Test Compounds

The pre-emergence activity of the compounds of the present invention is exemplified by the following test in which the seeds of a variety of monocotyledonous and dicotyledonous plants are separately mixed with potting soil and planted on top of approximately one inch of soil in separate pots. After planting the pots are sprayed with the selected aqueous acetone solution containing test compound in sufficient quantity to provide the equivalent of about 0.025 to 0.4 kg per hectare of test compound per pot. The treated pots are then placed on greenhouse benches, watered and cared for in accordance with conventional greenhouse procedures. From 2 to 4 weeks after treatment, the tests are terminated and each pot is examinated and rated according to the rating system set forth above.

| Rating System | % Difference in Growth from the check |
|---|---|
| 0 - No effect | 0 |
| 1 - Trace effect | 1–5 |
| 2-Slight effect | 6–15 |
| 3 - Moderate effect | 16–29 |
| 4-Injury | 30–44 |
| 5 - Definite injury | 45–64 |
| 6 - Herbicidal effect | 65–79 |
| 7 - Good herbicidal effect | 80–90 |
| 8 - Aproaching complete kill | 91–99 |
| 9- Complete kill | 100 |

The herbicidal proficiency of the active ingredients of the present invention is evident from the test results which are recorded in Table 1 below.

TABLE 1

Crop selectivity and weed control
(PRE-EMERGENCE APPLICATION)

| Cpd.-No. | dose rate kg/ha | ABUTH | IPOHE | LAMPU | MATIN | PAPRH | STEME | VERPE | SETVI | GLYMA | GOSHI | ORYSA | TRZAW | ZEAMX |
|---|---|---|---|---|---|---|---|---|---|---|---|---|---|---|
| 3 | 0.400 | 1 | 1 | 8 | 2 | 9 | 8 | 2 | 7 | 0 | 0 | 0 | 0 | 0 |
| 4 | 0.400 | 5 | 9 | 9 | 9 | 9 | 9 | 9 | 9 | 2 | 5 | 1 | 3 | 2 |
|   | 0.100 | 3 | 3 | 8 | 9 | 8 | 4 | 9 | 8 | 1 | 1 | 0 | 1 | 1 |
| 5 | 0.400 | 8 | 9 | 9 | 8 | 9 | 9 | 9 | 9 | 6 | — | 6 | 6 | 5 |
|   | 0.100 | 8 | 9 | 8 | 8 | 9 | 8 | 8 | 9 | 4 | 6 | 3 | 4 | 3 |
|   | 0.025 | 6 | 5 | 8 | 8 | 9 | 8 | 7 | 6 | 3 | — | 2 | 2 | 2 |
| 6 | 0.400 | 3 | 2 | 8 | 9 | 9 | 9 | 9 | 9 | 2 | 2 | 2 | 2 | 1 |
|   | 0.100 | 2 | 2 | 7 | 9 | 9 | 7 | 8 | 9 | 1 | 1 | 1 | 0 | 0 |
| standard | 0.300 | 0 | 0 | 0 | 0 | — | 0 | 0 | 0 | 0 | — | 0 | 0 | 0 |
|   | 0.150 | 0 | 0 | 0 | 0 | — | 0 | 0 | 0 | 0 | — | 0 | 0 | 0 |
|   | 0.075 | 0 | 0 | 0 | 0 | — | 0 | 0 | 0 | 0 | — | 0 | 0 | 0 |

— = not tested
X = assessment impossible

The compounds no. 3, 4 and 6 showed good selectivity in soybeans, maize, cotton and rice. In the case of compound no. 5 sufficiently good selectivity was recorded on rice, wheat and maize at the lowest dose of 0.025 kg/ha. All compounds of the invention displayed high levels of broad-leaved weed control. Compounds no. 4 and 5 exhibited in addition good control of the grass species *Setaria virides* at crop selective doses.

The compounds of the invention showed clearly superior activity over the standard which is 4-methyl-6-(4-fluorophenoxy)-2-(3-trifluoromethylphenyl)-pyrimidine being known from EP 0 723 960 A.

Post-emergence Herbicidal Evaluation of Test Compounds

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels equivalent of about 0.025 to 0.4 kg per hectare of test compound per pot. After spraying the plants are placed on greenhouse benches and are cared for in the usual manner, commensurate with conventional greenhouse practices. From 2 to 4 weeks after treatment, the seedling plants are examined and rated according to the rating system provided above. A rating 0 indicates growth as untreated check, a rating 9 indicates death. The results of the test are set out in Table 2 below.

TABLE 2

Crop selectivity and weed control
(POST-EMERGENCE APPLICATION)

| Cpd.-No. | dose rate kg/ha | CASOB | GALAP | PAPRH | STEME | VERPE | SETVI | TRZAW | ZEAMX |
|---|---|---|---|---|---|---|---|---|---|
| 3 | 0.400 | 9 | 6 | X | 8 | 8 | 5 | 2 | 2 |
|   | 0.100 | 8 | 4 | X | 6 | 8 | 4 | 1 | 2 |
| 4 | 0.400 | 7 | 9 | 9 | 9 | 9 | 9 | 2 | 3 |
|   | 0.100 | 7 | 9 | 9 | 8 | 9 | 8 | 1 | 2 |
|   | 0.025 | 5 | 9 | 7 | 6 | 9 | 4 | 1 | 2 |
| 5 | 0.025 | — | 5 | 7 | 5 | 8 | 6 | 2 | 2 |
| 6 | 0.400 | 6 | 9 | 6 | 9 | 9 | 9 | 2 | 3 |
|   | 0.100 | 6 | 5 | 4 | 6 | 9 | 4 | 1 | 3 |
| standard | 0.300 | — | 1 | 3 | 1 | 2 | 0 | 0 | 0 |
|   | 0.150 | — | 1 | 0 | 0 | X | 0 | 0 | 0 |
|   | 0.075 | — | 0 | 0 | 0 | 1 | 0 | 0 | 0 |

— = not tested
X = assessment impossible

In post-emergence application the compounds of the invention showed good selectivity in wheat and in general also in maize. They were quite active on broad-leaved weeds. Compounds no. 4 and 6 were the most active compounds on broad-leaved weeds. These two examples controlled the grass species *Setaria virides* at wheat selective doses in addition.

As already demonstrated in pre-emergence the compounds of the invention showed clearly superior activity over the standard which is 4-methyl-6-(4-fluorophenoxy)-2-(3-trifluoromethylphenyl)-pyrimidine being known from EP 0 723 960 A.

What is claimed is:

1. A compound of formula I:

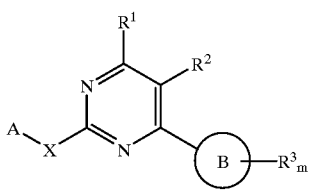

wherein A represents either
- I. a phenyl, 2-pyridyl, 3-pyridyl, 4-pyridyl, 2-pyrimidyl, 4-pyrimidyl or 5-pyrimidyl group, optionally substituted with one or more of either a halogen atom, or a $C_1$–$C_6$ alkyl, $C_1$–$C_4$ alkoxy, $C_1$–$C_4$ haloalkyl, $C_1$–$C_4$ haloalkoxy, $C_1$–$C_4$ alkylthio or $C_1$–$C_4$ haloalkylthio group; or
- II. a heterocycle selected from the group consisting of:

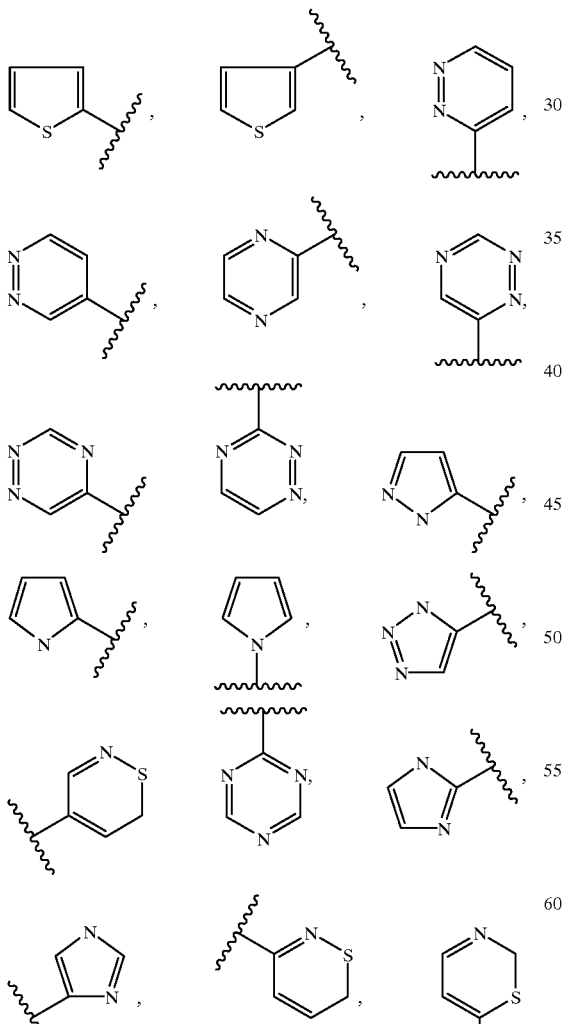

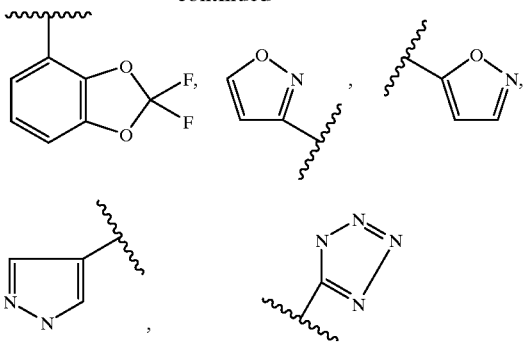

optionally substituted with one or two substituents selected from a halogen atom, or a $C_1$–$C_4$ alkyl or $C_1$–$C_4$ haloalkyl group;

B represents a phenyl, pyridyl or thienyl group;

m represents an integer from 0 to 5;

$R^1$ represents a halogen atom, a cyano group or a $C1$–$C_6$alkyl, alkenyl, alkynyl or alkoxyalkyl group, or a $C_1$–$C_4$haloalkyl, alkoxy, haloalkoxy, alkylthio, alkylamino or dialkylamino group;

$R^2$ represents a hydrogen or halogen atom, a cyano group, or a $C$–$C_6$alkyl or a $C_1$–$C_4$alkoxy, haloalkyl or haloalkoxy group;

$R^3$ (or each $R^3$) independently represents a halogen atom, a $C_1$–$C_6$alkyl, alkenyl or alkynyl group, a $C_1$–$C_4$alkoxy, $C_1$–$C_6$alkoxyalkyl, $C_1$–$C_6$alkoxyalkoxy, a $C_1$–$C_4$alkylthio, alkylsulphinyl, alkylsulphonyl group, a nitro, cyano, $C_1$–$C_4$haloalkyl, $C_1$–$C_4$haloalkoxy, $C_1$–$C_4$haloalkylthio or $SF_5$ group, the $C_1$–$C_6$ or $C_1$–$C_4$ group in one or more of the $R^1$ to $R^3$ groups, being optionally substituted by one or more substituents selected from phenyl, halogen atoms, nitro, cyano, hydroxyl, $C_1$–$C_4$alkoxy, $C_1$–$C_4$haloalkoxy and $C_1$–$C_4$alkoxycarbonyl groups, with the proviso that when B is phenyl, m is at least 1 and $R^3$ cannot be halogen, $C_1$–$C_6$ alkyl, $C_1$–$C_4$ alkoxy, nitro or cyano; and X represents an oxygen or sulfur atom.

2. A compound as claimed in claim 1, wherein A has a substituent in the meta-position relative to the point of attachment.

3. A compound as claimed in claim 2, wherein A is meta-substituted by a chlorine atom, or a trifluoromethyl, trifluoromethoxy or difluoromethoxy group.

4. A compound as claimed in claim 1, wherein $R^1$ is an alkoxy group.

5. A compound as claimed in claim 1, wherein X is oxygen.

6. A compound as claimed in claim 1, wherein B is a phenyl group, m is 1 or 2 and one of the groups $R^3$ is attached in the para-position relative to the point of attachment.

7. A compound as claimed in claim 1 selected from the group consisting of:

4-methoxy-2-(1'-methyl-3'-trifluoromethylpyrazol-5'-yloxy)-6-(4''-trifluoromethylphenyl)pyrimidine;

6-(4'-fluorophenyl)-4-methoxy-2-(1''-methyl-3''-trifluoromethylpyrazol-5'-yloxy)pyrimidine;

4-ethoxy-2-(1'-methyl-3'-trifluoromethylpyrazol-5'-yloxy)-6-(4''-trifluoromethylphenyl)pyrimidine;

4-methoxy-2-(3'-trifluoromethylphenoxy)-6-(4''-trifluoromethyl-phenyl)pyrimidine;

2-(2'-chloropyrid-4'-yloxy)-4-methoxy-6-(4"-trifluoromethyl-phenyl)pyrimidine;

2-(2'-difluoromethoxypyrid-4'-yloxy)-4-methoxy-6-(4"-trifluoromethyl-phenyl)pyrimidine;

2-(2'-trifluoromethylpyrid-4'-yloxy)-4-methoxy-6-(4"-trifluoromethyl-phenyl)pyrimidine;

4-methyl-2-(3'-trifluoromethylphenoxy)-6-(4"-trifluoromethyl-phenyl)pyrimidine;

4-methoxy-2-(1'-methyl-3'-trifluoromethylpyrazol-5'-yloxy)-6-(4"-trifluoro-methylthien-2"-yl)pyrimidine.

8. A herbicidal composition which comprises one or more compound as claimed in claim 1 and a carrier and/or a surface-active agent.

9. A method of combating undesired plant growth at a locus, which comprises treating the locus with an effective amount of one or more compound as claimed in claim 1.

10. A compound of formula I A

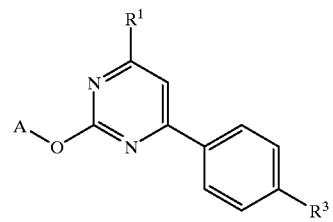

(IA)

wherein A represents 3-trifluoromethylphenyl, 2-chloropyrid-4-yl, 2-trifluoromethylpyrid-4-yl, 2-difluoromethoxypyrid4-yl, 5-trifluoromethylthien-3-yl or 1-methyl-3-trifluoromethylpyrazol-5-yl, $R^1$ is a $C_1$–$C_6$ alkyl group or a $C_1$–$C_4$ alkylthio or alkoxy group; $R^3$ represents a fluorine, chlorine or bromine atom, or a trifluoromethyl, trifluoromethoxy, difluoromethoxy or cyano group.

* * * * *